United States Patent [19]
Clark et al.

[11] Patent Number: 5,958,874
[45] Date of Patent: Sep. 28, 1999

[54] RECOMBINANT FIBRONECTIN-BASED EXTRACELLULAR MATRIX FOR WOUND HEALING

[75] Inventors: Richard A. Clark, Poquott, N.Y.; Doris Greiling, Deal, United Kingdom; James Gailit, Stony Brook, N.Y.

[73] Assignee: The Research Foundation of State University of New York, Albany, N.Y.

[21] Appl. No.: 09/025,706

[22] Filed: Feb. 18, 1998

[51] Int. Cl.$^6$ .......................... A01N 37/18; A61K 38/00; C07K 1/00
[52] U.S. Cl. .................... 514/2; 514/12; 514/950; 514/969; 530/300; 530/350; 530/810; 530/812
[58] Field of Search ................... 514/2, 12, 950, 514/969; 530/350, 300, 810, 812

Primary Examiner—Robert A. Wax
Assistant Examiner—Tekchand Saidha
Attorney, Agent, or Firm—Braman & Rogalskyj, LLP

[57] ABSTRACT

The invention provides an extracellular matrix for enhancing wound healing. The extracellular matrix comprises a recombinant fibronectin protein and a backbone matrix, wherein the recombinant fibronectin protein comprises peptides from two or more fibronectin domains. The extracellular matrix facilitates wound healing by providing hemostasis and, in addition, an environment that intrinsically recruits new tissue cells to the wound site. The extracellular matrix according to the subject invention is thus used in a method for enhancing wound healing. The method comprises applying the extracellular matrix to the wound.

24 Claims, 9 Drawing Sheets

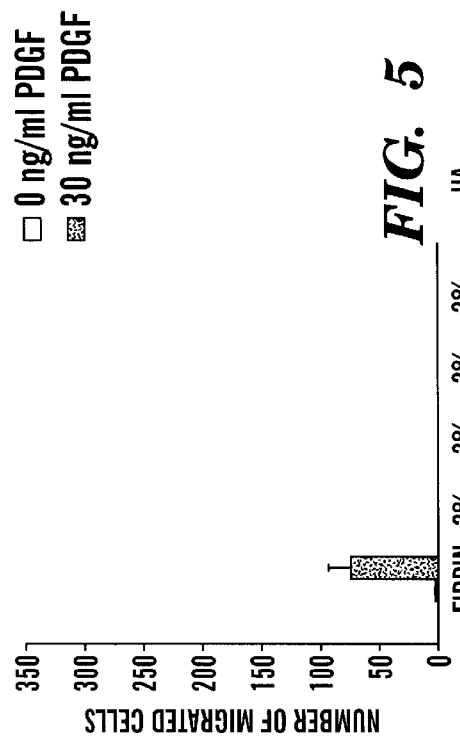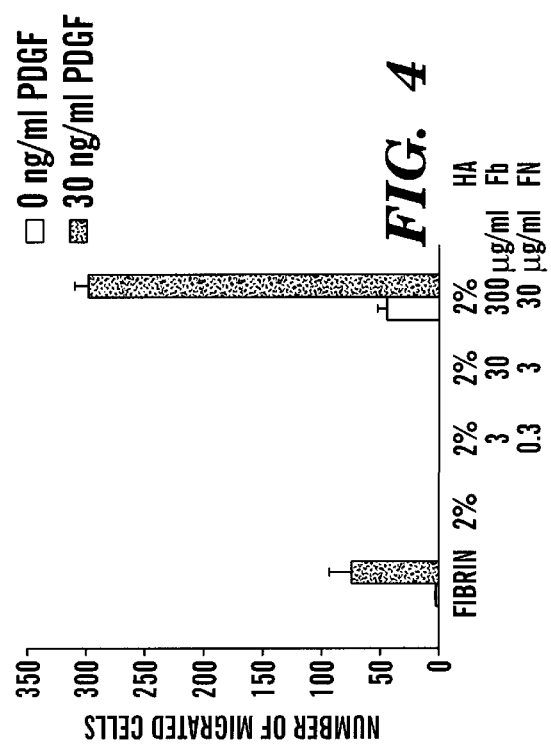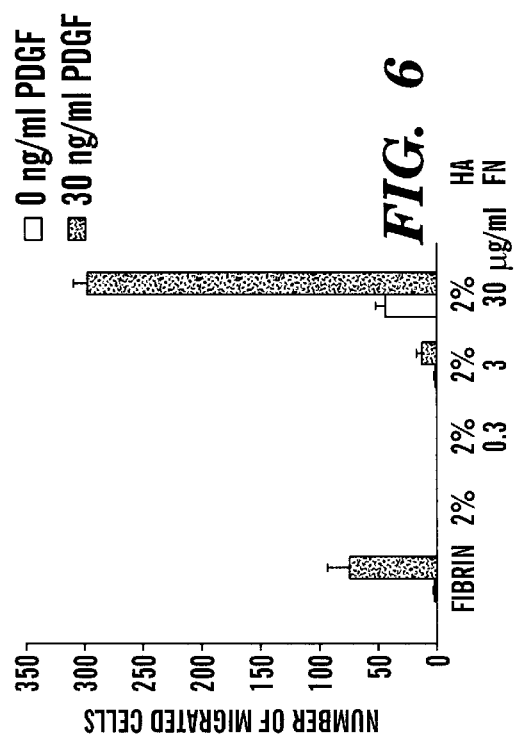
FIG. 4
FIG. 5
FIG. 6

RECOMBINANT FIBRONECTIN-BASED EXTRACELLULAR MATRIX FOR WOUND HEALING

The subject matter of this application was made with support from the United States Government under National Institutes of Health Grant No. AG 101143-12.

FIELD OF THE INVENTION

The subject invention is directed to an extracellular matrix for wound healing and to a method of enhancing wound healing using the extracellular matrix.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

It is estimated that in 1992 (U.S.), 35.2 million wounds required major therapeutic intervention (Medical Data International, Inc. 1993). Surgical incisional wounds are performed with aseptic technique, and are closed by primary intention. Most repair and heal uneventfully. Many traumatic wounds and cancer extirpations, however, must be left open to heal by secondary intention. Furthermore, chronic wounds have significant tissue necrosis and fail to heal by secondary intention. It is estimated that 5.5 million people in the U.S. have chronic, nonhealing wounds and that their prevalence is increasing secondary to the increase in age-related diseases, the increase in Acquired-immune Deficiency Syndrome (AIDS), and the increase of radiation wounds secondary to cancer intervention. In the U.S. approximately 1.5–2.5 million people have venous leg ulcers; 300,000–500,000, diabetic ulcers; and 2.5–3.5 million, pressure ulcers (Callam et al. 1987; Phillips and Dover 1991; Lees and Lambert 1992; Lindholm et al. 1992). These acute and chronic open wounds require long-term care and procedures that include skin grafting and tissue flaps, debridement, frequent dressing changes and administration of pain medications. This care is costly and labor intensive. Furthermore, these wounds have a severe impact on the patients' quality of life. The chronic dermal ulcerations can cost as much as $40,000 each to heal and more disappointing is that 50% reappear within 18 months of healing. Chronic dermal ulcers are also associated with mortality. As many as 21% of patients in intermediate-care facilities with pressure ulcers die (Bergstrom et al. 1994).

Although multiple millions of dollars have been spent on the development of numerous recombinant growth factors (Abraham and Klagsbrun 1996; Heldin and Westermark 1996; Nanney and King 1996; Roberts and Sporn 1996) and organotypic skin replacements (Boyce et al. 1995) for use in open wounds over the past decade, the evidence of cost-effective benefit is meager thus far (Brown et al. 1989; Robson et al. 1992a; Robson et al. 1992b; Phillips et al. 1993).

Many attempts have been made to produce a composition which can be used to facilitate wound repair. Many of these compositions involve collagen as a component. U.S. Pat. Nos. 4,950,483 and 5,024,841 each discuss the usefulness of collagen implants as wound healing matrices. U.S. Pat. No. 4,453,939 discusses a wound healing composition of collagen with a fibrinogen component and a thrombin component, and optionally fibronectin. U.S. Pat. No. 4,970,298 discusses the usefulness of a biodegradable collagen matrix (of collagen, hyaluronic acid, and fibronectin) for wound healing. Yamada et al. (1995) disclose an allogeneic cultured dermal substitute that is prepared by plating fibroblasts onto a spongy collagen matrix and then culturing for 7 to 10 days. Devries et al. (1995) disclose a collagen/alpha-elastin hydrolysate matrix that can be seeded with a stromal-vascular-fraction of adipose tissue. Lamme et al. (1996) disclose a dermal matrix substitute of collagen coated with elastin hydrolysate. U.S. Pat. No. 5,489,304 and Ellis and Yannas (1996) each disclose a collagen-glycosaminoglycan matrix.

There are also numerous compositions which involve hyaluronic acid (HA) as a component. Ortonne (1996), Borgognoni et al. (1996), and Nakamura et al. (1997) each discuss the usefulness of HA for wound healing. In Nakamura et al. (1997), the HA was combined with chondroitin sulfate in one series of experiments. In U.S. Pat. No. 5,604,200, medical grade HA and tissue culture grade plasma fibronectin were used in combination with calcium, phosphate, uric acid, urea, sodium, potassium, chloride and magnesium to create a moist healing environment that simulates the fetal in utero wound healing matrix. U.S. Pat. No. 5,631,011 discloses a composition of HA and fibrin or fibrinogen.

Various other compositions have also been explored for their wound healing capabilities. Kratz et al. (1997) used a gel of heparin ionically linked to chitosan. Bartold and Raben (1996) studied platelet-derived growth factor (PDGF). Henke et al. (1996) disclosed that chondroitin sulfate proteoglycan mediated cell migration on fibrinogen and invasion into a fibrin matrix, while Nakamura et al. (1997) concluded that chondroitin sulfate did not affect wound closure in a corneal epithelial wound. Henke et al. (1996) also disclosed that an anti-CD44 antibody blocked endothelial cell migration on fibrinogen. U.S. Pat. No. 5,641,483 discloses topical gel and cream formulations containing human plasma fibronectin for healing of cutaneous wounds. Schultz et al. (1992) disclose a composition of epidermal growth factor (EGF), fibronectin, a synthetic collagenase inhibitor, and Aprotinin.

Various studies involving fibronectin (FN) and/or particular fibronectin peptides and wound healing have also been reported. Many of these studies involve the RGD sequence, part of the cell binding domain of FN (see Schor et al. 1996; Steed et al. 1995; Sponsel et al. 1994; Kartha and Toback 1992; Kishida et al. 1992). Schor et al. (1996) disclose that only the gelatin binding domain of FN (GBD) stimulates fibroblast migration into a 3-D matrix of native type I collagen fibrils at femtomolar concentrations; whereas peptides of the other FN functional domains do not stimulate fibroblast migration in this assay at femtomolar to nanomolar concentrations. Schor et al. (1996) also disclose that the RGDS-containing cell binding domain of FN does, however, stimulate fibroblast migration in the transmembrane (or "Boyden chamber") assay. Steed et al. (1995) disclose that the RGD peptide matrix (known as Argidene Gel™ or as Telio-Derm Gel™) promoted wound healing. On the contrary, Sponsel et al. (1994) disclose that an RGD peptide impaired healing of a mechanical wound made in a confluent monolayer of one epithelial cell line. Kartha and Toback (1992) also concluded that an RGDS peptide completely inhibited cell migration into a wound area. Kishida et al. (1992), however, disclose that an RGD-albumin conjugate adsorbed onto a polyurethane sponge exhibited tissue ingrowth-promoting activity.

Other portions of FN have also been studied for wound healing activity. U.S. Pat. No. 5,198,423 studied the effects of a polypeptide containing a cell binding domain and a heparin binding domain of FN on wound healing. U.S. Pat. No. 4,589,881 studied the effects of a 108 aa polypeptide fragment of FN on wound healing, as well as a biologically active fragment thereof. Sponsel et al. (1994) studied the effect of the tetrapeptide REDV and the peptide LDVPS on wound healing.

The severity of the problem of chronic, nonhealing wounds dictates that continual efforts be made to define new and more effective matrices and methods for facilitating wound healing.

SUMMARY OF THE INVENTION

This need is met by the subject invention which provides an extracellular matrix for enhancing wound healing. The extracellular matrix comprises a recombinant fibronectin protein and a backbone matrix, wherein the recombinant fibronectin protein comprises peptides from two or more fibronectin domains. The extracellular matrix facilitates wound healing by providing an environment that intrinsically recruits new tissue cells to the wound site.

The extracellular matrix according to the subject invention is thus used in a method for enhancing wound healing. The method includes providing the extracellular matrix, and applying the extracellular matrix to the wound.

BRIEF DESCRIPTION OF THE DRAWINGS

These and other features and advantages of this invention will be evident from the following detailed description of preferred embodiments when read in conjunction with the accompanying drawings in which:

FIG. 4 illustrates the effect on cell migration of increasing concentrations of fibrin and fibronectin together;

FIG. 5 illustrates the effect on cell migration of increasing concentrations of fibrin;

FIG. 6 illustrates the effect on cell migration of increasing concentrations of fibronectin;

DETAILED DESCRIPTION OF THE INVENTION

The subject invention provides an extracellular matrix for wound healing comprising a recombinant fibronectin protein and a backbone matrix, wherein the recombinant fibronectin protein comprises peptides from two or more fibronectin domains. As used herein, an "extracellular matrix" refers to a scaffold in the cell's external environment with which the cells may interact via specific cell surface receptors. As further used herein, a "wound" is intended to include both acute and chronic dermal wounds including, for example, surgical incisional wounds, traumatic wounds, cancer extirpations, radiation wounds, venous leg ulcers, diabetic ulcers, and pressure ulcers.

The extracellular matrix according to the subject invention comprises a recombinant fibronectin protein and a backbone matrix, wherein the recombinant fibronectin protein comprises peptides from two or more fibronectin domains. These components are necessary for the subject extracellular matrix to enhance (e.g. improve, increase) wound repair, although additional components may also be included in the extracellular matrix. These additional components, such as platelet-derived growth factor as discussed below, may further enhance the beneficial effects of the extracellular matrix on wound healing.

Enhancement (e.g. improvement, increasing) of wound healing refers to the traditional sense of wound healing where clean closure of the wound occurs. Since naturally occurring wound healing involves the movement of fibroblasts into the wound site, enhancement of wound healing can be assayed in vitro using the model for cell transmigration provided in copending, co-assigned U.S. Ser. No. 08/723,789, filed Sep. 30, 1996 (the contents of which are incorporated by reference herein). Briefly, the model provides a contracted collagen gel containing fibroblasts surrounded by a fibrin gel (see FIG. 1). When the extracellular matrix of the subject invention replaces or is added to the fibrin gel, fibroblast movement from the collagen gel into the extracellular matrix or modified fibrin gel is enhanced compared to movement into the "gold standard" fibrin gel.

Figure 7:
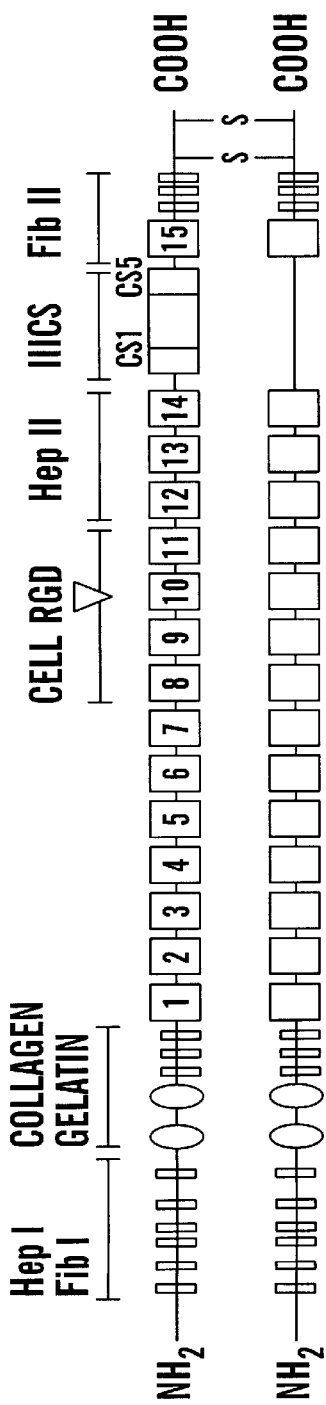
FIG. 7 illustrates the general structure of fibronectin, showing the number and relative positions of the basic functional domains.

The extracellular matrix of the subject invention comprises a recombinant fibronectin protein and a backbone matrix, wherein the recombinant fibronectin protein comprises peptides from two or more fibronectin domains. Fibronectin is a multi-domain, multifunctional cell adhesion protein found in blood and in a variety of tissue extracellular matrices (Yamada and Clark 1996). Although encoded by only a single gene, FNs exist in a number of variant forms that differ in sequence at three general regions of alternative splicing of its precursor mRNA. Some of this alternative splicing involves cell adhesion sequences, thereby providing a post-transcriptional mechanism for potentially regulating cell interaction. Nevertheless, all FN molecules appear to consist of the same basic functional domains. As shown in FIG. 7, these domains include two heparin binding domains, Hep I and Hep II; two fibrin binding domains, Fib I and Fib II; a collagen or gelatin binding domain; a cell-binding domain; and a variably splice IIICS domain, which contains within it CS1 and CS5 subdomains. Each domain is composed of FN repeats denoted as thin rectangles for the type 1 repeats, ovals for the type 2 repeats, and wide rectangles for the type 3 repeats.

As used herein, the "recombinant fibronectin protein" is constructed to comprise peptides from two or more fibronectin domains selected from the domains indicated above. As further used herein, a "recombinant fibronectin protein" is not intended to include a full-length recombinant fibronectin molecule; the recombinant fibronectin protein of the subject invention is smaller in size and therefore readily mixed with a backbone matrix, and generally includes only segments of the carboxy terminus of the fibronectin molecule. Where desirable, the recombinant fibronectin protein can, alternatively, be conjugated to the backbone matrix. Preferably, the segments of the carboxy terminus include two or more fibronectin domains selected from the type III repeats (the wide rectangles in FIG. 7) or the IIICS region. Suitable peptides that together form the recombinant fibronectin protein include the cell binding domain (such as peptides including the amino acid sequence SEQ ID NO:1: and peptides including the amino acid sequence SEQ ID NO:2:), the IIICS domain (such as peptides including the amino acid sequence SEQ ID NO:3 which is a truncated CS1 peptide; or the peptide designated CS1 and having an amino acid sequence as shown in SEQ ID NO:4; or the peptide designated CS5 and having an amino acid sequence as shown in SEQ ID NO:5), and the heparin II binding domain (such as the peptide designated H-I and having an amino acid sequence as shown in SEQ ID NO:6; or the peptide designated H-II and having an amino acid sequence as shown in SEQ ID NO:7; or the peptide designated H-III and having an amino acid sequence as shown in SEQ ID NO:8; or the peptide designated H-IV and having an amino acid sequence as shown in SEQ ID NO:9; or the peptide designated H-V and having an amino acid sequence as shown in SEQ ID NO:10; or the peptide having an amino acid sequence as shown in SEQ ID NO:11 {a COOH-terminal Hep-II peptide that binds $\alpha 4\beta$}).

As further used herein, a "backbone matrix" refers to natural extracellular matrices as well as biocompatible synthetic polymers. These backbone matrices provide the scaffold of the extracellular matrix and when the recombinant fibronectin protein is mixed with or conjugated to the backbone matrix, cells can move around on the scaffold. According to this invention, the recombinant fibronectin protein is constructed to include the peptides necessary for cell movement; by providing the peptides as a larger recombinant fibronectin protein, the protein can be mixed with the backbone matrix without a need to conjugate (in contrast, the small peptide molecules by themselves would diffuse away). However, conjugation of the recombinant FN protein to the backbone matrix may be desirable. Nevertheless, the recombinant FN protein is still much easier to work with than the large intact full-length fibronectin molecule.

There are numerous examples of backbone matrices suitable for use in the subject invention. These examples include fibrin, hyaluronic acid, polyethylene glycol, poly-L-glycol, and poly-L-lactate. Hyaluronic acid is commercially available as a dry (for example, lyophilized) powder, and can be reconstituted to a hyaluronic acid gel (in accordance with manufacturer's suggestions) for use in the subject invention. Depending upon the viscosity desired, a hyaluronic acid gel having about 5 milligrams to about 50 milligrams of hyaluronic acid per milliliter of reconstituting solution can be used. At 5 milligrams/milliliter, the hyaluronic acid gel will be more liquid, and at 50 milligrams/milliliter the hyaluronic acid gel will become more viscous and less easy to manipulate. The use of the gel will, in part, dictate the desired viscosity. If the extracellular matrix can be "poured" into and contained in a wound area, then a more liquid form of the hyaluronic acid gel will be satisfactory. If the extracellular matrix is "spread" over and/or into a wound area, then a more viscous form of the hyaluronic acid gel will be desirable. In either case, a dressing of some form will often cover the applied extracellular matrix to help prevent contamination and infection of the wound. It should be readily apparent that the extracellular matrix itself (and each of its components) must be sterile (free of biological and/or chemical contamination) to also prevent contamination and infection of the wound, and biocompatible to prevent adverse tissue reaction.

Preferably, the hyaluronic acid gel is provided as a gel having about 20 milligrams of dry hyaluronic acid per milliliter of reconstituting solution. Suitable reconstituting solutions include, for example, sterile distilled water, sterile phosphate buffered saline (PBS), or a cell culture medium.

As used herein, "hyaluronic acid" is intended to include the various forms of hyaluronic acid (HA) known in the art. These various forms include HA chemically modified (such as by cross-linking) to vary its resorbtion capacity and/or its ability to be degraded. Optimal HA formulations will be resorbable in a few days to a week.

Having identified the peptides from two or more fibronectin domains that will form the recombinant fibronectin protein, the recombinant fibronectin protein can be constructed using genetic engineering techniques. The resulting recombinant fibronectin protein can be stored as a dry (for example, lyophilized) powder, and can be reconstituted to a fibronectin solution (in accordance with manufacturer's suggestions) for use in the subject invention. Preferably, the stock fibronectin solution is prepared with one milligram of dry fibronectin per milliliter of fibronectin reconstituting solution (such as, for example, sterile distilled water). The final concentration of fibronectin in the backbone matrix is preferably about 10 micrograms to about 100 micrograms of fibronectin per milliliter of backbone matrix. More preferably, the final concentration is about 30 micrograms of fibronectin per milliliter of backbone matrix.

In a further embodiment of the subject invention, the extracellular matrix further includes platelet-derived growth factor (PDGF). The PDGF may be provided at a final concentration of about 1 nanogram to about 100 nanograms of PDGF per milliliter of backbone matrix; more preferably, at a final concentration of about 30 nanograms of PDGF per milliliter of backbone matrix.

The invention further provides a method of enhancing wound healing which comprises applying the extracellular matrix (as described herein) to a wound. As discussed above, the method of applying the extracellular matrix to the wound may vary depending on the type and location of the wound as well as the viscosity of the extracellular matrix. Preferably, the extracellular matrix is viscous enough to be "spread" over the wound and will not run off after application.

Materials and Methods

Normal Human Dermal Fibroblasts

Primary cultures of human adult dermal fibroblasts, acquired from Marcia Simon (Living Skin Bank, SUNY at Stony Brook), the ATCC (Bethesda, Md.), or the NIA (Bethesda, Md.), are cultured in Dulbecco's modified Eagle's medium (DMEM, Life Technologies) containing 42 mM sodium bicarbonate and supplemented with 100 U/ml penicillin, 100 µg/ml streptomycin, and 10% fetal bovine serum (FBS, HyClone, Logan, Utah), at 37° C. and 5% $CO_2$/95% air in an humidified atmosphere. The cells are used between passages 4 and 12.

Fibroblast Migration Assays: Transmigration from Organotypic Collagen Gel Constructs into Fibrin/Fibronectin Gels or Outmigration Over Protein coated surfaces

Preparation of Floating, Contracted Collagen Gels

Fibroblast cultures at 80% confluence are harvested by treatment with 0.05% trypsin/0.01% EDTA. Trypsin is inactivated by addition of soy bean trypsin inhibitor in PBS containing 0.2% BSA. The cells are washed twice with DMEM+2% BSA and resuspended at a concentration of $1 \times 10^6$ cells/ml. The fibroblasts are mixed with neutralized collagen (Vitrogen 100, Celtrix Labs., Santa Clara, Calif.), 2% BSA, 30 ng/ml PDGF-BB, 30 μg/ml fibronectin, and concentrated DMEM so that the final concentration of DMEM and sodium bicarbonate is 1×. 600 μl of the cell mixture is added to the wells of a 24-well tissue culture plate, which has been precoated with 2% BSA. The collagen is allowed to polymerize at 37° C. The final concentration of collagen is 1.8 mg/ml and each gel contains $6 \times 10^4$ cells. After two hours incubation, the gels are gently detached from the plastic surface to allow contraction with the addition of 0.5 ml DMEM+2% BSA and 30 ng/ml PDGF-BB per well. The gels are incubated overnight at 37° C. in 100% humidity, 5% $CO_2$ and 95% air.

Preparation of Protein Coated Wells

Fibronectin, its fragments or recombinant domains were diluted with concentrated DMEM to the appropriate concentration. Aliquots of 450 μl protein solution are added to the wells of 24-well tissue culture plates (Becton-Dickinson, Lincoln Park, N.J.). After a 2 hour incubation at 37° C. in 5% $CO_2$, plates were dried overnight at room temperature under sterile conditions.

Preparation of Two-Dimensional Outmigration Model

Plates coated with dried proteins were washed once with PBS and incubated with 2% BSA for 1 hour at 37° C. to block nonspecific binding sites. After washing the plates three times with PBS, contracted-collagen gel organotypic constructs were attached to the coated plates. DMEM, 2% BSA and 30 ng/ml PDGF-BB was added to assay plates so that the medium was level with the top of the collagen gel.

Preparation of Three-Dimensional Transmigration Model

For preparation of "gold standard" transmigration assays containing a dermal organotypic construct surrounded by a fibrin clot as previously described (Greiling and Clark 1997), dried fibrin fibril-coated dishes are washed once with PBS and fibroblast-contracted collagen gels are placed on the surface. Fibrinogen, at a final concentration of 300 μg/ml, is mixed with DMEM and 1.0 U/ml thrombin, added to the wells so that the solution is level with the top of the collagen gel, and allowed to clot at room temperature for 30 min. When needed, other supplements such 30 ng/ml PDGF-BB, are added to the mixture. For HA 3-dimensional transmigration, wells are coated overnight at 37° C. with an appropriate solution of HA. The next day a fibroblast-contracted collagen gel is placed on the HA-coated well in DMEM, with or without 30 ng/ml PDGF-BB, is added so that the solution is level with the top of the collagen gels. All migration assays are quantified after a 24 hours incubation at 37° C. in 100% humidity, 5% $CO_2$ and 95%.

Evaluation of Cell Migration

The number of migrated cells was quantified under a Nikon inverted phase microscope by visually counting identifiable cell nuclei located outside of the contracted collagen gel in the fibrin gel (transmigration assay) or on the matrix (out migration assay). Within a given experiment each condition was run in triplicate and means±SD calculated. All experiments were repeated at least three times. Statistical differences among conditions can be determined by ANOVA.

Fibroblast Adhesion Assay

Assay plates are prepared as described under fibroblast migration assays. The assay for measuring fibroblast adhesion to matrix proteins are performed essentially as described (Gailit et al. 1993) except that the cell concentration is lowered to 100,000 cells/ml or 10,000 cells/well. Cells are allowed to attach for 60 min at 37° C. before the unattached cells are washed away and the attached cells fixed with 2% glutaraldehyde. After fixation, attached cells are air dried at room temperature and then 100 ml of 0.1% crystal violet in 0.2 M boric acid, pH 9, is added to each well and the microtiter plate shaken at 600 rpm on a plate mixer for 20 minutes. (The staining solution is prepared fresh from a stock solution of 5% crystal violet in 20% methanol.) Excess stain is removed by three washes with water. The stained cells are again air dried before the crystal violet is solubilized by adding 100 ml of 10% acetic acid to each well and then shaking the plate at 600 rpm for 20 minutes. The absorbance at 590 nm is measured with a dual wavelength microtiter plate reader (THERMOmax, Molecular Devices, Menlo Park, Calif.) and the reading corrected for light scattering by subtraction of the absorbance at 450 nm.

EXAMPLE I

Assay of Wound Healing

Figure 1:
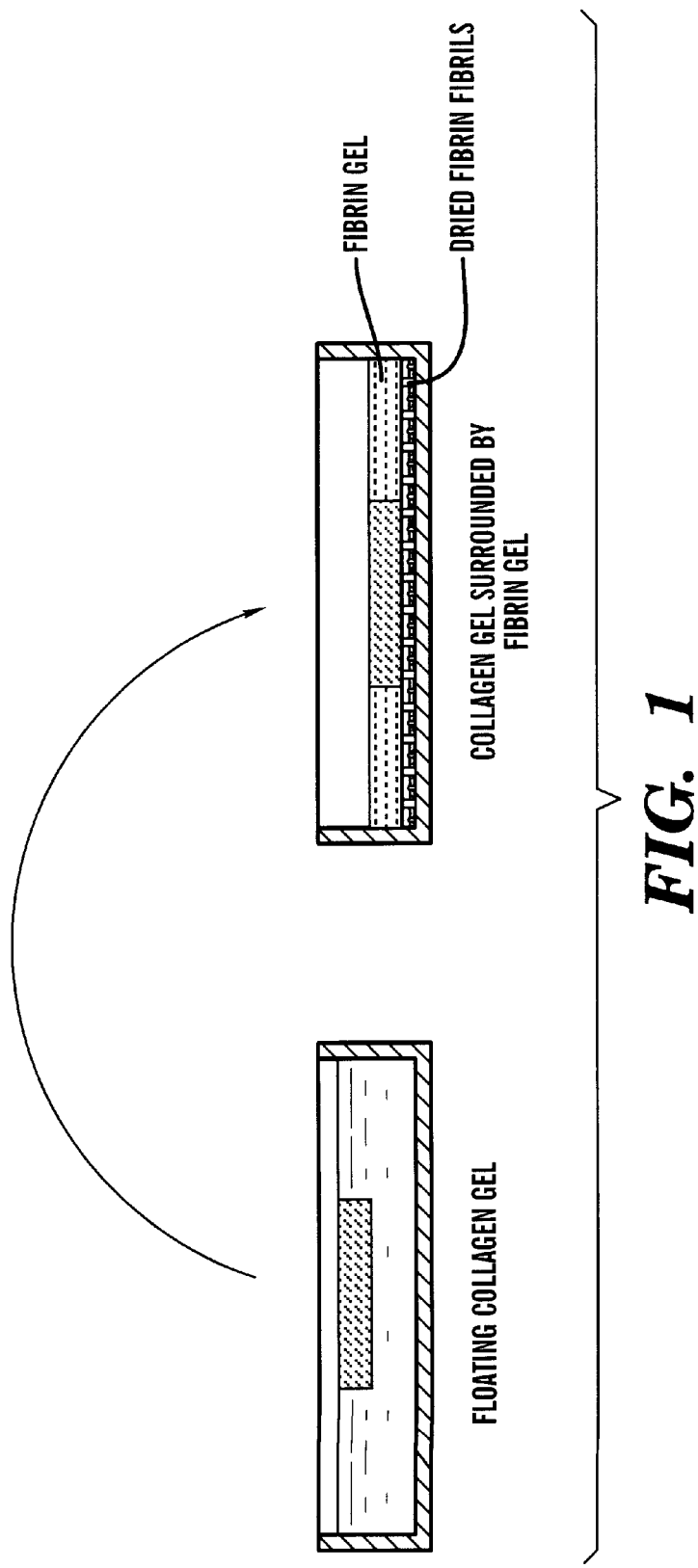
FIG. 1 illustrates the in vitro model for assaying cell transmigration from a collagen gel into a fibrin gel.

The extracellular matrix of the present invention was tested by use of the in vitro model as described in U.S. patent application Ser. No. 08/723,789, which is hereby incorporated by reference. The basis of the in vitro model is a contracted collagen gel containing fibroblasts which acquire a tissue-like phenotype within the collagen matrix. Surrounding the collagen gel, or dermal equivalent, with a fibrin clot produces a simple inside-outside model of the early cutaneous wound (FIG. 1). Without an added stimulus, no more than a few of the normal adult human dermal fibroblasts within the collagen gel migrate into the fibrin gel. However, the transmigration of fibroblasts from the collagen gel into the fibrin gel is enhanced by the replacement of the fibrin gel with the extracellular matrix of the subject invention or by the addition of the recombinant fibronectin protein to a fibrin gel backbone matrix, since the two or more FN domains facilitate cell movement thereby enhancing wound healing.

EXAMPLE II

Using the 3-dimensional transmigration assay described above, the matrix of the subject invention was modeled. These experiments led to the conclusion that fibronectin (FN) can enhance human dermal fibroblast movement from a collagen gel into a fibrin gel or a hyaluronic acid (HA) gel.

Figure 15A:
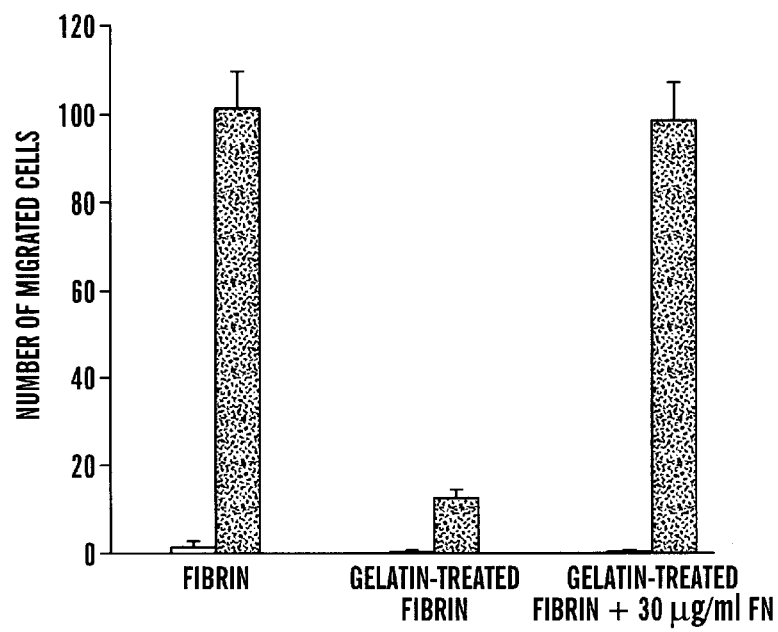
FIGS. 15A–15B illustrate the requirement of fibronectin for transmigration.

Initially, experiments were conducted to determine whether FN, either in a fibrin gel or in a collagen gel, is required for fibroblast transmigration. To do this, FN was selectively removed from each matrix material. First, residual FN was removed from the fibrinogen preparation by affinity chromatography on gelatin. After removal of FN, fibroblast transmigration into the fibrin clot was decreased by about 80% (FIG. 15A). Transmigration could be restored by the addition of FN to the fibrin gel. Optimal cell movement was observed with 30 μg/ml, a FN:fibrinogen ratio of 1:10, the physiological plasma ratio. In FIG. 15A, migration induced by 30 ng/ml PDGF-BB (shaded bars; open bars: 0 35 ng/ml PDGF) was measured under the usual assay conditions. The fibrinogen preparation used to form the fibrin gel was untreated (left), treated with gelatin-Sepharose to remove FN (center), or treated with gelatin-Sepharose and then supplemented with 30 μg/ml FN (right).

Figure 15B:
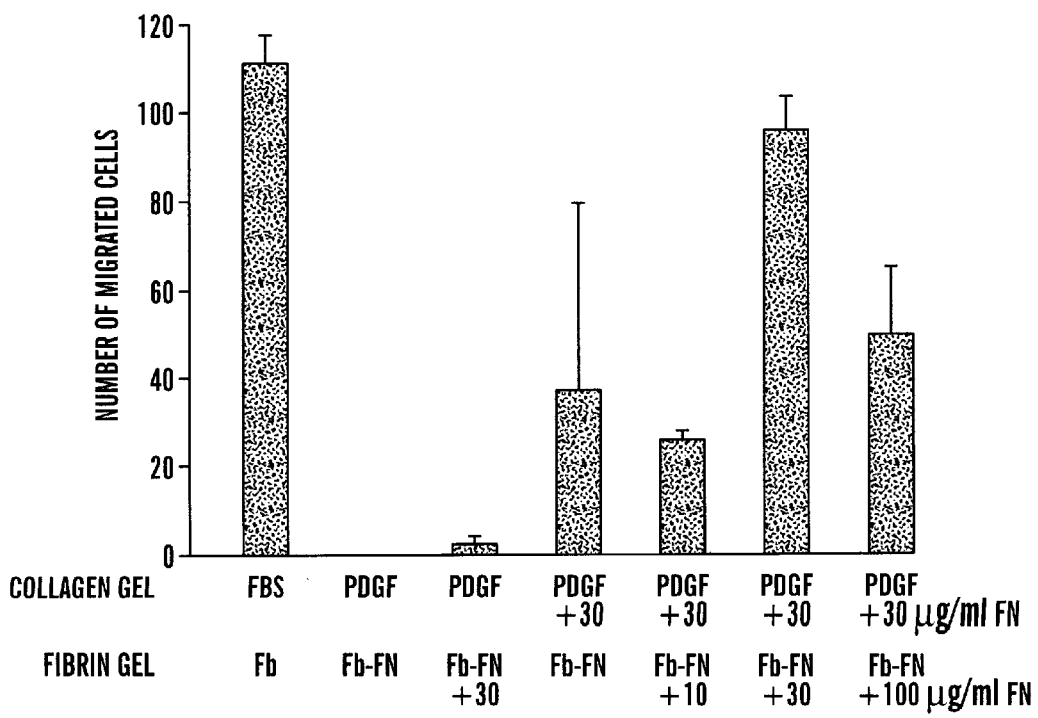

Second, exogenous FN was excluded from the collagen gel by omitting serum and substituting PDGF-BB, which is equally effective at stimulating fibroblast-driven collagen gel contraction. In experiments with FN-free collagen gels no transmigration occurred (FIG. 15B). Transmigration was only observed when FN was present in both the collagen gel and the fibrin gel; 30 μg/ml FN in each gel seemed the most effective. In FIG. 15B, migration induced by 30 ng/ml PDGF-BB (shaded bars) was measured under modified assay conditions. Contraction of the collagen gel was stimulated with serum as usual (FBS) or with 30 ng/ml PDGF-BB (PDGF). The fibrinogen preparation used to form the fibrin gel was untreated (Fb), treated with gelatin-Sepharose to remove FN (Fb-FN), or treated with gelatin-Sepharose and then supplemented with 10, 30, or 100 μg/ml FN. The inclusion of 30 μg/ml FN in the collagen gel and in the fibrin gel restored transmigration to a normal level.

Figure 2:
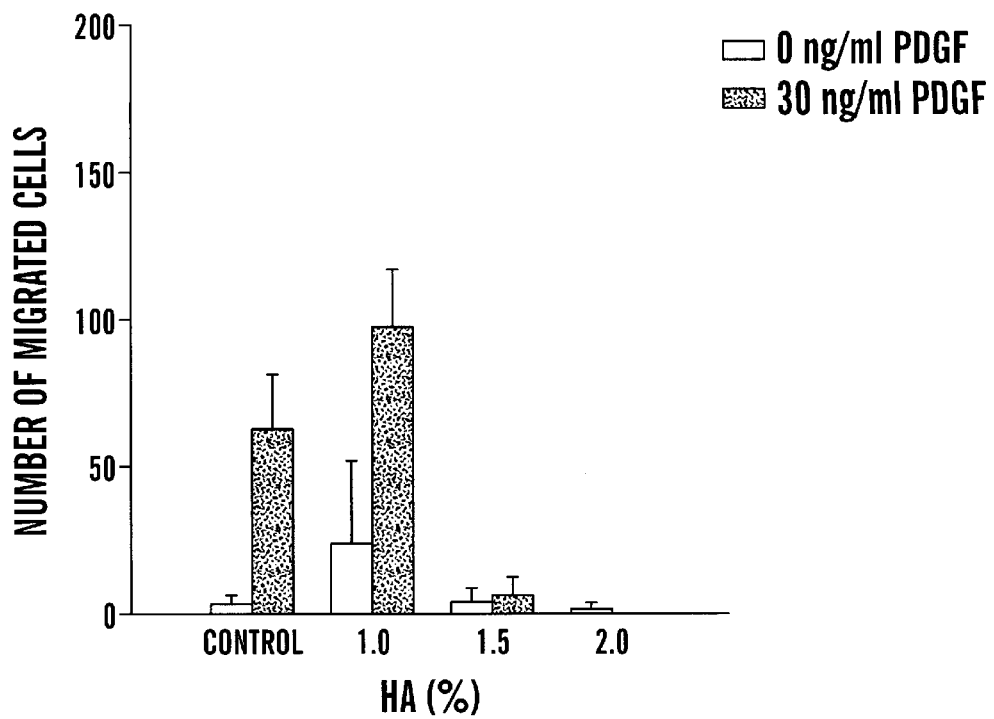
FIG. 2 illustrates the effect on cell migration of varying concentrations of pure hyaluronic acid.
Figure 3:
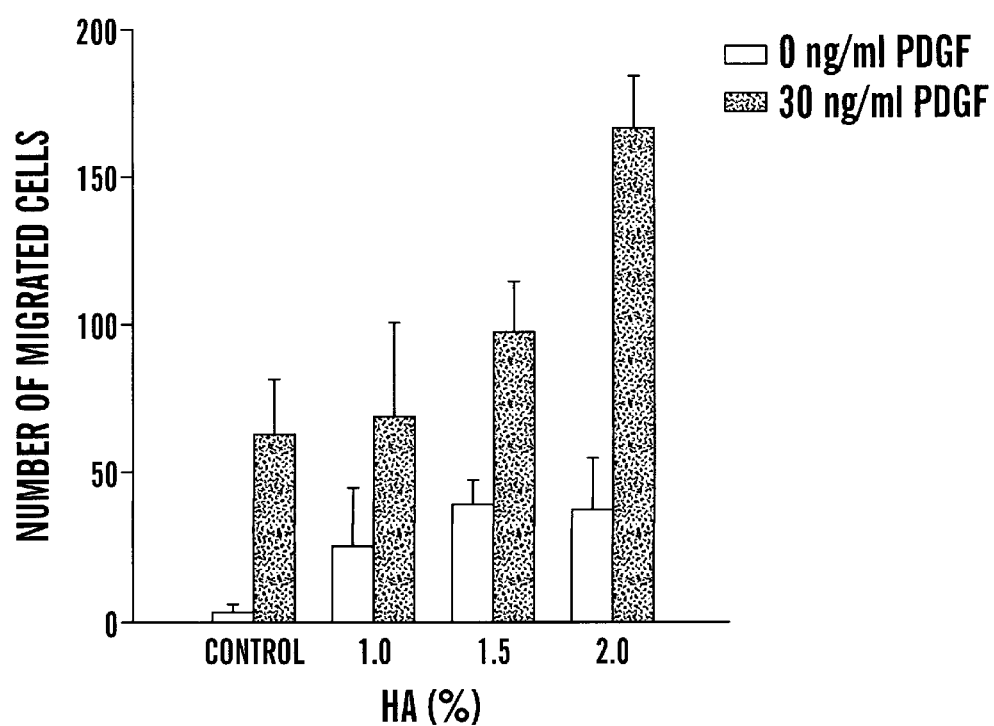
FIG. 3 illustrates the effect on cell migration when 300 µg/ml fibrin containing 30 µg/ml fibronectin is added to varying concentrations of hyaluronic acid.

Experiments were then conducted to determine whether FN is required for fibroblast transmigration from a collagen gel into a hyaluronic acid gel. At first, different concentrations of pure HA were placed around the organotypic collagen construct (FIG. 2). When stimulated with 30 ng/ml PDGF-BB, fibroblast migrated into a 1% HA semi-liquid somewhat better than a control fibrin matrix, composed of 300 μg/ml purified fibrin and 30 μg/ml FN. However, no migration was observed into 1.5% and 2% HA gels. When 300 μg/ml fibrin containing 30 μg/ml FN was added to the three concentrations of HA, a progressive increase in cell migration was seen (FIG. 3). About 3-fold more cells invaded the 2% HA/fibrin/FN formulation than the fibrin/FN control.

Since both fibrin and FN were present in HA gel formulations that supported robust cell movement, experiments were then conducted to determine which additive was needed for the enhanced migration. Increasing concentrations of fibrin and FN together (FIG. 4), fibrin alone (FIG. 5), or FN alone (FIG. 6) were added to 2% HA gels. As can be seen in FIG. 4, a minimum concentration of 300 μg/ml fibrin and 30 μg/ml FN was required for fibroblast transmigration into the 2% HA gel. Fibrin alone at concentrations up to 300 μg/ml added to 2% HA did not sustain cell movement (FIG. 5), however, 30 μg/ml FN added to 2% HA supported migration that was 4-fold greater than that observed in fibrin/FN clots (FIG. 6).

EXAMPLE III

Fibronectin (FN) is required for fibroblast migration through both fibrin clots and hyaluronic acid (HA) gels. Therefore, the FN domains necessary for migration were examined.

Figure 8:
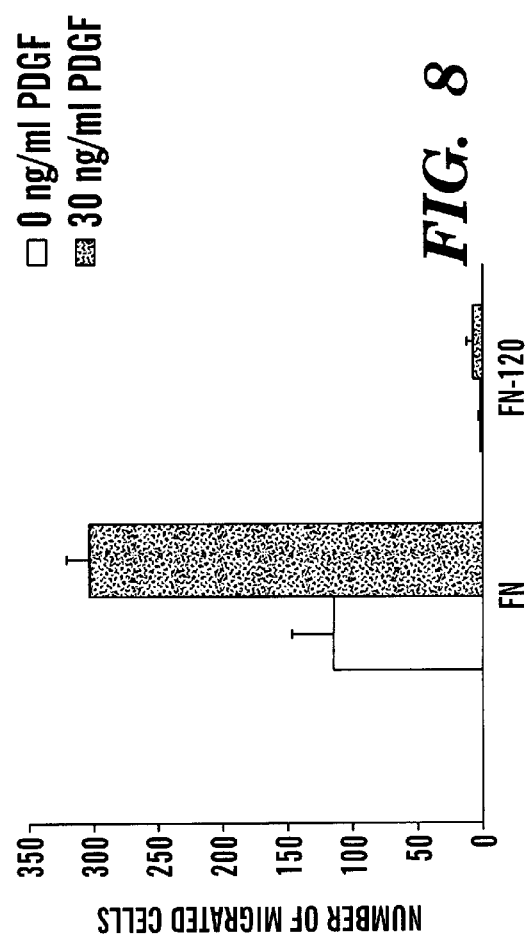
FIG. 8 illustrates the effect on cell migration of FN and FN-120 with or without PDGF.

In the first experiment focused on the specific sequences of the FN molecule necessary for migration of fibroblasts, assay wells were coated with 120 nmol/l of either intact FN (FN) or the 120 kDa fragment of FN (FN-120). The FN-120 fragment was isolated from a chymotrypsin digest as previously described (Wikner and Clark 1988). FN-120 contains the RGDS cell-binding peptide and the PHSRN synergy peptide, but lacks the Hep II and IIICS domains (see FIG. 9). Surprisingly, although FN-120 promotes 70% adhesion of fibroblasts compared to intact FN, it does not allow migration (FIG. 8). Reduction and alkylation of FN dimer to the monomeric state did not affect its ability to mediate either adhesion or migration.

Figure 9:
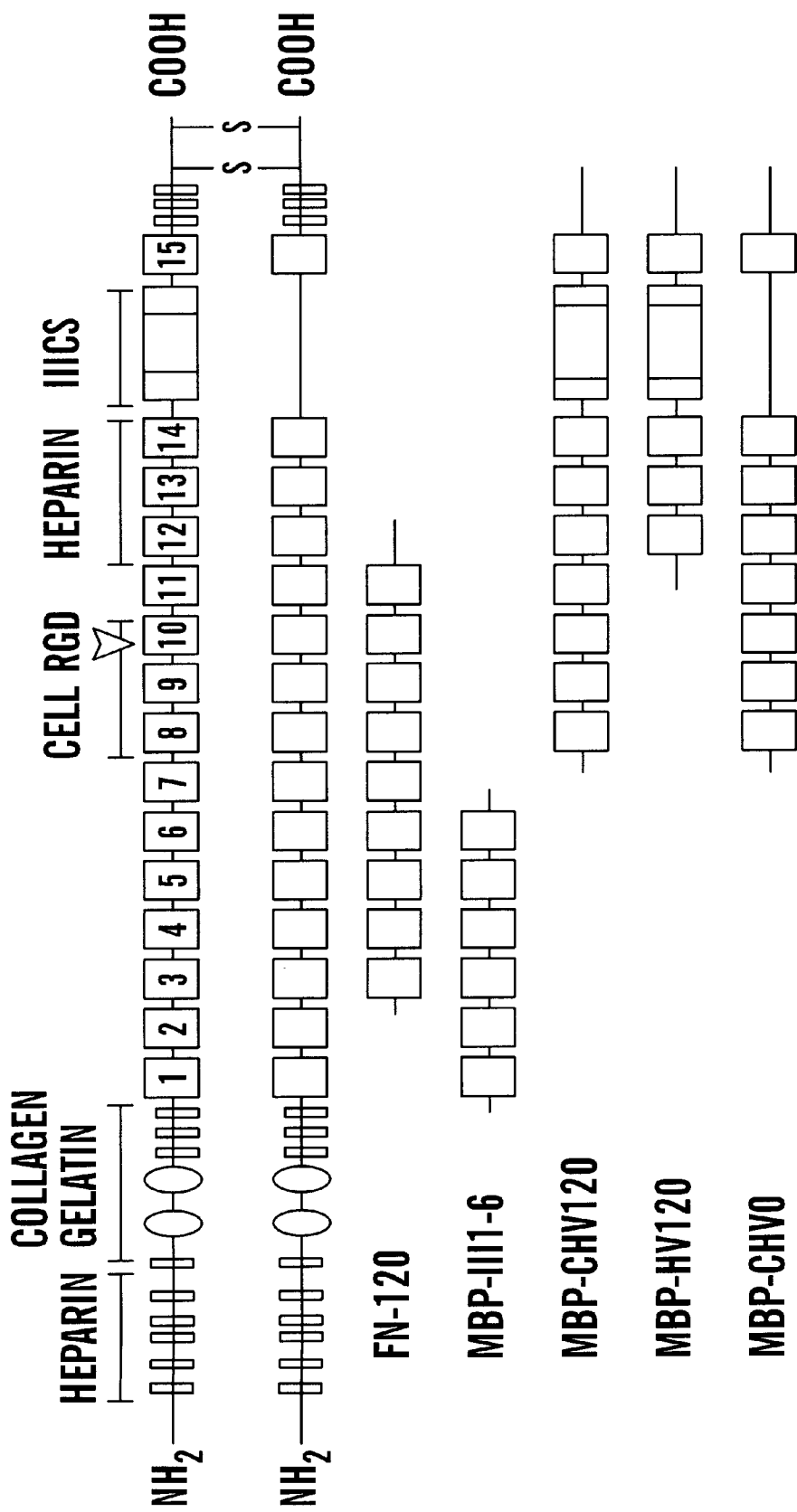
FIG. 9 illustrates the relation of the various recombinant FN proteins to the domains of FN.
Figure 10A:
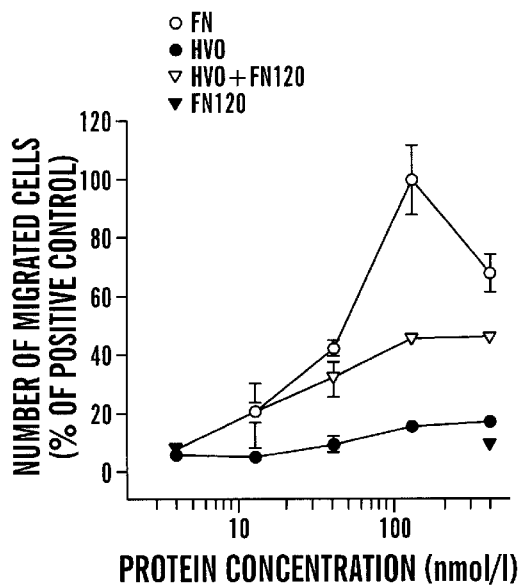
FIGS. 10A–10D illustrate the effect on cell migration of various recombinant FN proteins.
Figure 10B:
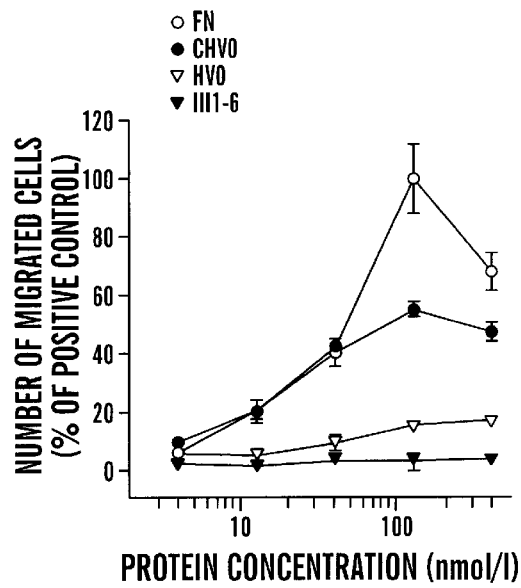

Next, the Hep II domain was examined for its ability to support migration. For this purpose a variety of recombinant FN proteins were obtained from Jean Schwartzbauer at Princeton University (Barkalow and Schwarzbauer 1991) (FIG. 9). Referring to FIG. 9, recombinant proteins are indicated by MBP. Assay plates were coated with 4 to 400 nmol/l of FN, FN-120 or recombinant proteins by drying the protein solution overnight at room temperature. The coating efficiency of all proteins was essentially the same as judged by the bicinchoninic acid protein assay (Tuszynski and Murphy 1990). A recombinant Hep II domain (HV0) supported migration at a level less than 20% of the migration observed on intact FN (FIG. 10A). Addition of FN-120 and HV0 on these plates, which presented both the RGD cell-binding and heparin-binding domains, respectively, in a non contiguous array, enhanced fibroblast migration to approximately 45% of the maximum level seen with intact FN (FIG. 10A). When recombinant FN protein CHV0, which contains both the RGD cell- and the heparin-binding domains in one molecule (FIG. 9), was used to coat the plates approximately 55% of the maximum level of migration was attained (FIG. 10B). Thus, about the same level of migration occurred whether the RGD cell- and heparin-binding domains were available to the cells in contiguous, or non contiguous, arrangments. Neither the FN-120 fragment alone, nor a control recombinant peptide III1–6, containing the 1st through the 6th FN type III repeats without known cell-binding sites (FIG. 9), allowed any migration (FIGS. 10A and 10B).

Figure 10C:
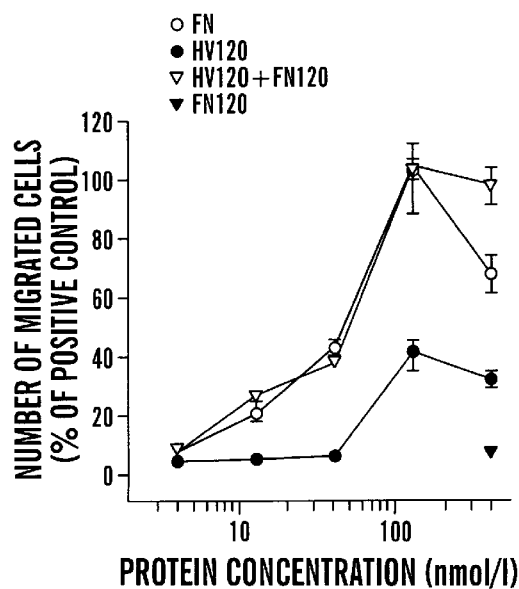
Figure 10D:
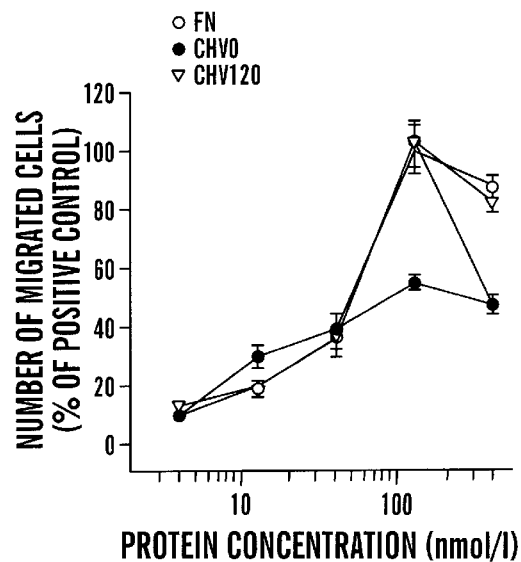

Next, experiments were conducted to examine whether the Hep II domain combined with the IIICS domain, which contains classic α4β1 binding sites, supports more migration than the Hep II domain alone. To this end, a recombinant protein HV120 containing both these domains (FIG. 9) was added to the surface of assay plates. As shown in FIG. 10C, HV120 supported 40% of the maximal migration observed with intact FN. However, when plates were coated with HV120, containing the heparin-binding and IIICS domains, and the FN-120 FN fragment, containing the RGD cell-binding peptide, migration comparable to that on intact FN was observed (FIG. 10C). When a recombinant protein CHV120, which contains the RGD-cell binding domain, the heparin-binding domain and the IIICS domain within one molecule (FIG. 9), was used to coat assay plates, essentially the same result was obtained; that is, maximal levels of migration were seen compared to migration on intact FN (FIG. 10D).

Figure 11:
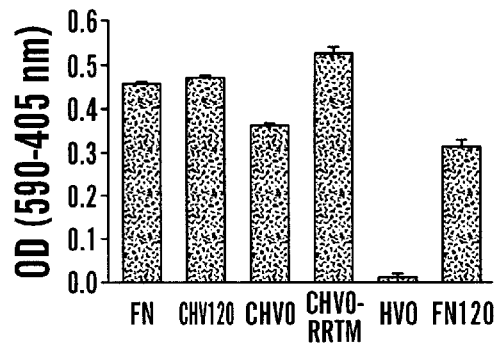
FIG. 11 illustrates the levels of fibroblast adhesion for various FN peptides.

Migration supported with CHV0 (about 55% maximum, FIG. 10B) was completely abolished if the arginine-pair XX in the 13th type III FN repeat of the Hep II domain was mutated to uncharged amino acids (CHV0-RR-TM) as previously described (Barkalow and Schwarzbauer 1991). In contrast, CHV0-RR-TM supported fibroblast adhesion at levels comparable to intact FN, CHV120 and CHV0 (FIG. 11).

Figure 12:
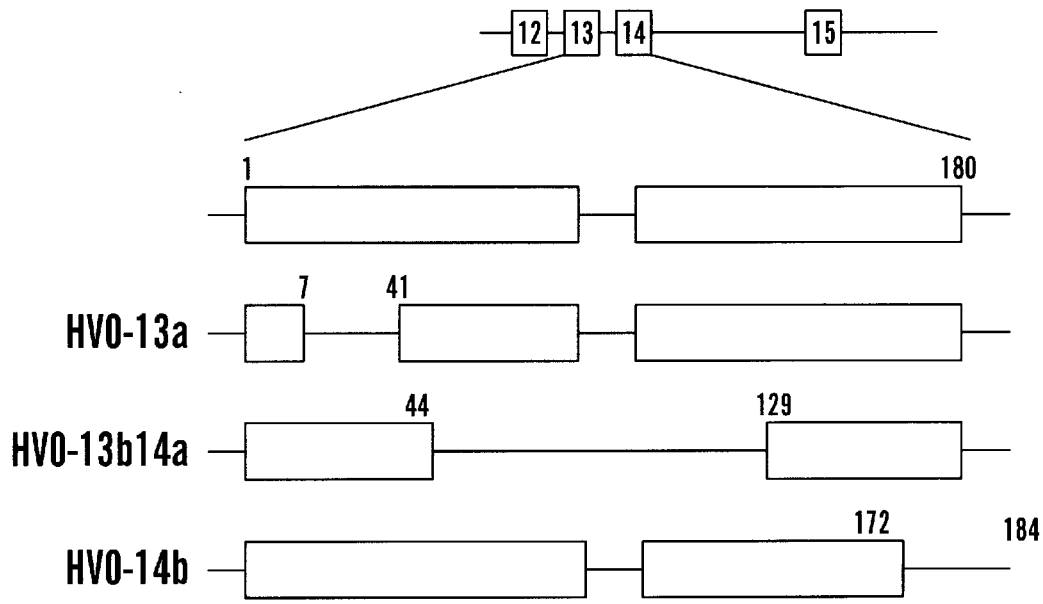
FIG. 12 illustrates the relation of various deletion mutants of the Hep II domain to the Hep II domain of FN.

These results lead to the conclusion that short, specific sequences within the Hep II domain are absolutely necessary for cell motility. To address this, deletion mutants of the Hep II domain were investigated (HV0-13a, HV0-13b14a, and HV0-14b, which were missing selected sequences of amino acids in the 13th and 14th type III repeats as shown in FIG. 12 and previously described (Barkalow and Schwarzbauer 1991; Barkalow and Schwarzbauer 1994)). HV0 and its mutants supported little migration by themselves at concentrations up to 400 nmol/l (Table 1). Furthermore, the addition of FN-120 along with the Hep II deletion mutants to the assay plates did not enhance migration (Table 1). In contrast, when FN-120 was added to the assay plates in combination with the entire recombinant Hep II domain (HV0) migration was enhanced (Table 1 and FIG. 10A). These results confirm the conclusion that multiple subdomains within the Hep II domain are required for optimal cell migration.

Figure 13:
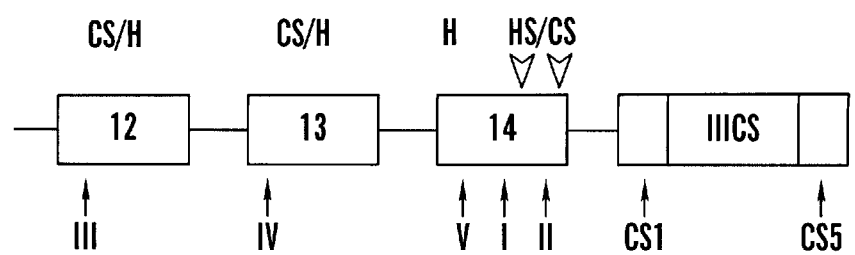
FIG. 13 illustrates the relation of various synthetic peptides to the Hep II and IIICS domains of FN.

To further define which Hep II and IIICS subdomains are involved in fibroblast migration on FN, synthetic peptides previously shown to be active in cell adhesion were manufactured from sequences in the 12th, 13th, and 14th FN type III repeats (peptides I, II, III, IV, and V)(McCarthy et al. 1988; McCarthy et al. 1990; Drake et al. 1993; Mooradian et al. 1993) and the IIICS segment (CS1 and CS5) (Humphries et al. 1987; Komoriya et al. 1991; Mould et al. 1991)(FIG. 13). FN peptide I (FN-C/HI; SEQ ID NO:6 YEKPGSPRREVVPRPRGV), peptide V (FN-C/HV; SEQ ID NO:10 WQPPRARI), CS1 (SEQ ID NO:3), and CS1i (i=inactive, SEQ ID NO:12) were purchased from Peninsula Laboratories Inc. (Belmont, Calif.). FN peptide II (FN-C/HII; SEQ ID NO:7), peptide III (FN-C/HIII; SEQ ID NO:8), peptide IV (FN-C/HIV; SEQ ID NO:9), and CS5 (SEQ ID NO:5) were synthesized by SynPep (Dublin, Calif.). The purity of all peptides was higher than 97%.

Figure 14A:
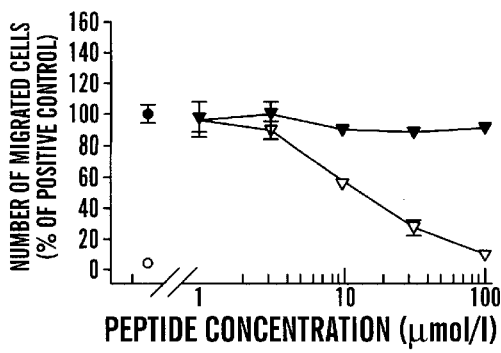
FIGS. 14A–14H illustrate the effect on cell migration of various synthetic peptides.
Figure 14B:
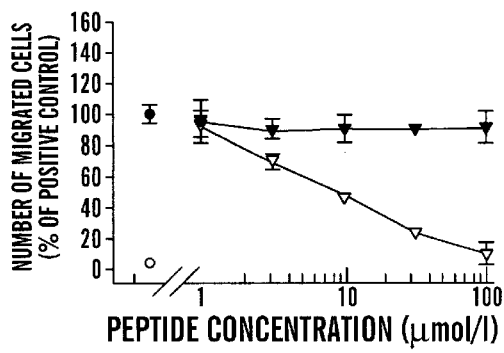
Figure 14C:
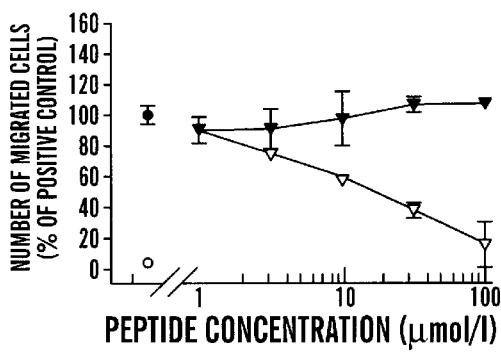
Figure 14D:
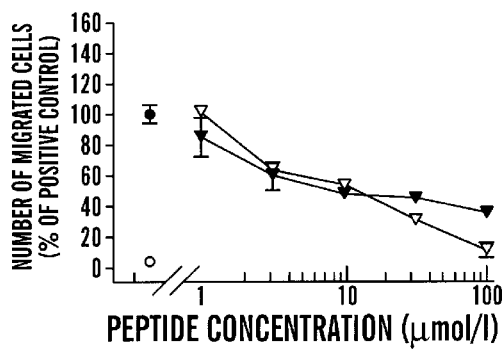
Figure 14E:
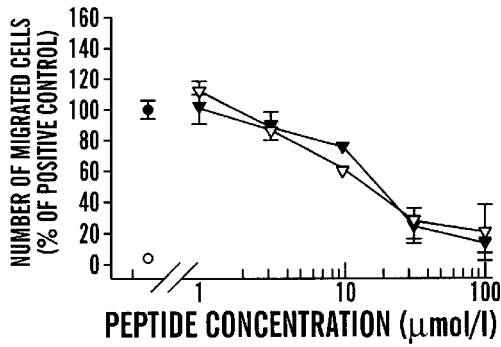
Figure 14F:
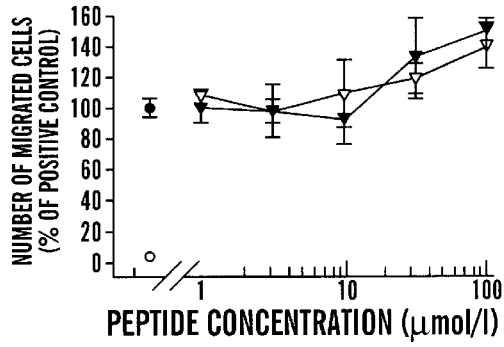
Figure 14G:
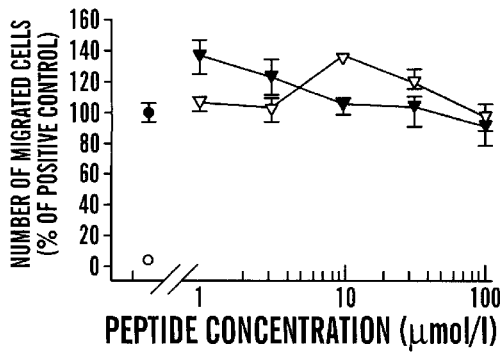
Figure 14H:
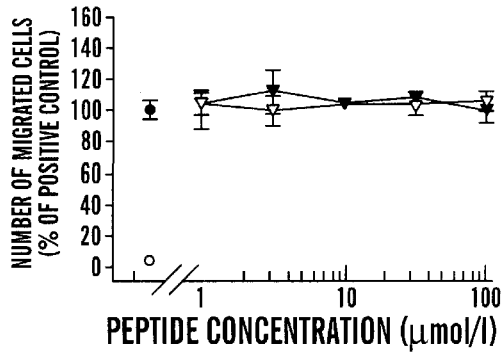

When added to the outmigration assay, peptides III (FIG. 14A), IV (FIG. 14B), V (FIG. 14C), I (FIG. 14D), and II (FIG. 14E) inhibited the migration of fibroblasts onto dried FN in a dose-dependent manner. CS1 (FIG. 14F) had a slightly enhancing effect in the higher concentrations while CS5 did not influence the migration at the tested concentrations (FIG. 14G). A control scrambled peptide of CS1 (CS1i), did not influence migration (FIG. 14H). To determine whether the observed effect of synthetic peptides on the migration was specific for FN, collagen coated assay plates were substituted for FN coated plates. Peptides III (FIG. 14A), IV (FIG. 14B), and V (FIG. 14C) had no effect on migration over collagen while peptides I and II (FIG. 14D and 14E, respectively) had an inhibitory effect in a dose-dependent manner. CS5 enhanced the migration at higher concentrations (FIG. 14G) while CS1i did not influence the activity (FIG. 14H).

To determine whether the results obtained from the two-dimensional outmigration assay related to more complex, 3-dimensional transmigration, the same synthetic peptides were added to the fibrin/FN gel in the transmigration assay. Most peptides gave essentially the same results. In aggregate these data demonstrate that 3 major domains of FN are required for fibroblast migration.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

|  | no additional protein added to plates | +FN-120 |
| --- | --- | --- |
| FN[a] | 100 ± 2.7[b] |  |
| HV0 | 15.3 ± 1.1[c] | 45.4 ± 1.1 |
| HV0-13a | 23.3 ± 1.7 | 23.3 ± 2.2 |
| HV0-13b14a | 6.3 ± 2.4 | 8.7 ± 4.8 |
| HV0-14b | 20.1 ± 2.0 | 15 ± 3.7 |

[a]All proteins and peptides were assayed at concentrations from 3 to 400 nmol/l, however, maximum fibroblast migration was observed when 120 nmol/l protein was added to assay plates. Therefore, the data shown were acquired from plates coated with 120 nmol/l FN, recombinant peptides or FN-120.
[b]Fibroblast migration on fibronectin (FN) was normalized to 100%.
[c]Data are presented as mean ± SD percent migration of that observed on FN. All conditions were run in triplicate.

REFERENCES

Abraham, J. A., and Klagsbrun, M., in "The Molecular and Cellular Biology of Wound Repair", 2d edition, Clark, R. A. F., ed, Plenum Press, New York, N.Y. (1996).

Barkalow, F. J., and Schwarzbauer, J. E., J Biol Chem 266(12):7812–7818 (1991).

Barkalow, F. J., and Schwarzbauer, J. E., J Biol Chem 269(6):3957–3962 (1994).

Bartold, P. M., and Raben, A., J Periodontal Research 31(3):205–216 (1996).

Bergstrom, N., et al., "Treatment of Pressure Ulcers", U.S. Department of Health and Human Services, Clinical Practice Guideline, Vol. 15, Rockville, Md. (1994).

Borgognoni, L., et al., Euro J Dermatology 6(2):127–131 (1996).

Boyce, S. T., et al., Ann Surg 222:743–752 (1995).

Brown, G. L., et al., N Eng J Med 321:76–79 (1989).

Callam, M. J., et al., Br med J 294:1389–1391 (1987).

Devries, H. J. C., et al., Laboratory Investigation 73(4):532–540 (1995).

Drake, S. L., et al., J Biol Chem 268(21):15859–15867 (1993).

Ellis, D. L., and Yannas, I. V., Biomaterials 17(3):291–299 (1996).

Gailit, J., et al., J Invest Dermat 100:323–328 (1993).

Greiling, D., and Clark, R. A. F., J Cell Sci 110:861–870 (1997).

Heldin, C.-H., and Westermark, B., in "The Molecular and Cellular Biology of Wound Repair", 2d edition, Clark, R. A. F., ed, Plenum Press, New York, N.Y., pp 249–274 (1996).

Henke, C. A., et al., J Clin Investigation 97(11):2541–2552 (1996).

Humphries, M. J., et al., J Biol Chem 262:6886–6892 (1987).

Kartha, S., and Toback, F. G., J Clinical Investigation 90(1):288–292 (1992).

Kishida, A., et al., Biomaterials 13(13):924–930 (1992).

Komoriya, A., et al., J Biol Chem 266(23):15075–15079 (1991).

Kratz, G., et al., Scandinavian J of Plastic and Reconstructive Surgery and Hand Surgery 31(2):119–123 (June 1997).

Lamme, E. N., et al., J Histochemistry and Cytochemistry 44(11):1311–1322 (1996).

Lees, T. A., and Lambert, D., Br J Surg 79:1032–1034 (1992).

Lindholm, C., et al., Acta Derm Venereol (Stockh) 72:227–230 (1992).

McCarthy, J. B., et al., Biochem 27:1380–1388 (1988).

McCarthy, J. B., et al., J Biol Chem 110:777–787 (1990).

Medical Data International, Inc., "Wound Card in the U.S.: Emerging trends, management and new product development" (1993).

Mooradian, D. L., et al., Invest Ophthalmol Vis Sci 34(1):153–164 (1993).

Mould, A. P., et al., J Biol Chem 266:3579–3585 (1991).

Nakamura, M., et al., Experimental Eye Research 64(6):043–1050 (1997).

Nanney, L. B., and King, L. E., in "The Molecular and Cellular Biology of Wound Repair", 2d edition, Clark, R. A. F., ed, Plenum Press, New York, N.Y., pp 171–194 (1996).

Ortonne, J. P., J Dermatological Treatment 7(2):75–81 (1996).

Phillips, L. G., et al., Ann Plast Surg 31:331–334 (1993).

Phillips, T. J., and Dover, J. S., J Am Acad Dermatol 25:965–987 (1991).

Roberts, A. B., and Sporn, M. B., in "The Molecular and Cellular Biology of Wound Repair", 2d edition, Clark, R. A. F., ed, Plenum Press, New York, N.Y., pp 275–310 (1996).

Robson, M. C., et al., Ann Surg 216:401–406 (1992a).
Robson, M. C., et al., Ann Plast Surg 29:193–201 (1992b)
Schor, S. L., et al., J Cell Science 109:2581–2590 (1996).
Schultz, G., et al., Acta Ophthalmologica 70(S202):60–66 (1992).
Sponsel, H. T., et al., Am J Physiology 267(2):F257–F264 (1994).
Steed, D. L., et al., Diabetes Care 18(1):39–46 (1995).
Tuszynski, G. P., and Murphy, A., Anal Biochem 184:189–191 (1990).

Wikner, N. E., and Clark, R. A. F., Methods in Enzymology 162:214–222 (1988).
Yamada, N., et al., Scandinavian J of Plastic and Reconstructive Surgery and Hand Surgery 29(3):211–219 (1995).
Yamada, K. M., and Clark, R. A. F., in "The Molecular and Cellular Biology of Wound Repair", 2d edition, Clark, R. A. F., ed, Plenum Press, New York, N.Y., pp 51–93 (1996).

What is claimed is:

1. An extracellular matrix for wound healing comprising a recombinant fibronectin protein and a backbone matrix, wherein the recombinant fibronectin protein comprises peptides from at least three fibronectin domains, the three fibronectin domains being the cell binding domain, the IIICS domain, and the heparin II binding domain.

2. The extracellular matrix of claim 1 wherein the cell binding domain includes the amino acid sequence SEQ ID NO:1.

3. The extracellular matrix of claim 1 wherein the cell binding domain includes the amino acid sequence SEQ ID NO:2.

4. The extracellular matrix of claim 1 wherein the IIICS domain includes the amino acid sequence SEQ ID NO:3.

5. The extracellular matrix of claim 1 wherein the IIICS domain includes a peptide designated CS1 having an amino acid sequence as shown in SEQ ID NO:4.

6. The extracellular matrix of claim 1 wherein the IIICS domain includes a peptide designated CS5 having an amino acid sequence as shown in SEQ ID NO:5.

7. The extracellular matrix of claim 1 wherein the heparin II binding domain includes a peptide designated H-I having an amino acid sequence as shown in SEQ ID NO:6.

8. The extracellular matrix of claim 1 wherein the heparin II binding domain includes a peptide designated H-II having an amino acid sequence as shown in SEQ ID NO:7.

9. The extracellular matrix of claim 1 wherein the heparin II binding domain includes a peptide designated H-III having an amino acid sequence as shown in SEQ ID NO:8.

10. The extracellular matrix of claim 1 wherein the heparin II binding domain includes a peptide designated H-IV having an amino acid sequence as shown in SEQ ID NO:9.

11. The extracellular matrix of claim 1 wherein the heparin II binding domain includes a peptide designated H-V having an amino acid sequence as shown in SEQ ID NO:10.

12. The extracellular matrix of claim 1 wherein the heparin II binding domain includes a peptide having an amino acid sequence as shown in SEQ ID NO:11.

13. The extracellular matrix of claim 1 wherein the backbone matrix comprises hyaluronic acid.

14. The extracellular matrix of claim 13 wherein the hyaluronic acid is provided as a gel having about 20 milligrams of dry hyaluronic acid per milliliter of reconstituting solution, and wherein the recombinant fibronectin protein is added to the hyaluronic acid gel for a final concentration of about 10 micrograms to about 100 micrograms of recombinant fibronectin protein per milliliter of hyaluronic acid gel.

15. The extracellular matrix of claim 14 wherein the recombinant fibronectin protein is added to the hyaluronic acid gel for a final concentration of about 30 micrograms of recombinant fibronectin protein per milliliter of hyaluronic acid gel.

16. The extracellular matrix of claim 13 wherein the hyaluronic acid is provided as a gel having about 5 milligrams to about 50 milligrams of dry hyaluronic acid per milliliter of reconstituting solution.

17. The extracellular matrix of claim 16 wherein the hyaluronic acid is provided as a gel having about 20 milligrams of dry hyaluronic acid per milliliter of reconstituting solution.

18. The extracellular matrix of claim 1 wherein the backbone matrix comprises polyethylene glycol.

19. The extracellular matrix of claim 1 wherein the backbone matrix comprises poly-L-glycol.

20. The extracellular matrix of claim 1 wherein the backbone matrix comprises poly-L-lactate.

21. The extracellular matrix of claim 1 wherein the recombinant fibronectin protein is provided as a solution having about 1 milligram of dry recombinant fibronectin protein per milliliter of fibronectin reconstituting solution.

22. The extracellular matrix of claim 1 wherein the recombinant fibronectin protein is conjugated to the backbone matrix.

23. The extracellular matrix of claim 1 further comprising platelet-derived growth factor.

24. A method of enhancing wound healing which comprises applying the extracellular matrix of claim 1 to a wound.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 3 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

Arg Gly Asp
   1

(2) INFORMATION FOR SEQ ID NO:2:

(i) SEQUENCE CHARACTERISTICS:
      (A) LENGTH: 5 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:2:

Pro His Ser Arg Asn
   1           5

(2) INFORMATION FOR SEQ ID NO:3:

(i) SEQUENCE CHARACTERISTICS:
      (A) LENGTH: 8 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:3:

Glu Ile Leu Asp Val Pro Ser Thr
   1           5

(2) INFORMATION FOR SEQ ID NO:4:

(i) SEQUENCE CHARACTERISTICS:
      (A) LENGTH: 25 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:4:

```
        Asp Glu Leu Pro Gln Leu Val Thr Leu Pro His Pro Asn Leu His Gly
        1               5                   10                  15

Pro Glu Ile Leu Asp Val Pro Ser Thr
                    20                  25

(2) INFORMATION FOR SEQ ID NO:5:

(i) SEQUENCE CHARACTERISTICS:
         (A) LENGTH: 20 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:5:

Gly Glu Glu Ile Gln Ile Gly His Ile Pro Arg Glu Asp Val Asp Tyr
     1               5                   10                  15

His Leu Tyr Pro
                 20

(2) INFORMATION FOR SEQ ID NO:6:

(i) SEQUENCE CHARACTERISTICS:
         (A) LENGTH: 18 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:6:

Tyr Glu Lys Pro Gly Ser Pro Arg Arg Glu Val Val Pro Arg Pro Arg
     1               5                   10                  15

Gly Val (2) INFORMATION FOR SEQ ID NO:7:

(i) SEQUENCE CHARACTERISTICS:
         (A) LENGTH: 15 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:7:

Lys Asn Asn Gln Lys Ser Glu Pro Leu Ile Gly Arg Lys Lys Thr
     1               5                   10                  15

(2) INFORMATION FOR SEQ ID NO:8:

(i) SEQUENCE CHARACTERISTICS:
         (A) LENGTH: 16 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:8:

Tyr Arg Val Arg Val Thr Pro Lys Glu Lys Thr Gly Pro Met Lys Glu
     1               5                   10                  15

(2) INFORMATION FOR SEQ ID NO:9:

(i) SEQUENCE CHARACTERISTICS:
```

```
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:9:

Ser Pro Pro Arg Arg Ala Arg Val Thr
        1               5

(2) INFORMATION FOR SEQ ID NO:10:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:10:

Trp Gln Pro Pro Arg Ala Arg Ile
        1               5

(2) INFORMATION FOR SEQ ID NO:11:

(i) SEQUENCE CHARACTERISTICS:
            (A) LENGTH: 19 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:11:

Val Val Ile Asp Ala Ser Thr Ala Ile Asp Ala Pro Ser Asn Leu Arg
        1               5                   10                  15

Phe Leu Ala (2) INFORMATION FOR SEQ ID NO:12:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:12:

Glu Ile Leu Glu Val Pro Ser Thr
        1               5
```